United States Patent [19]

Marsh

[11] 4,172,315

[45] Oct. 30, 1979

[54] METHOD OF MANUFACTURING A MAGNETIC FIELD SENSITIVITY INDICATOR APPARATUS FOR EVALUATING MAGNETIC FIELDS IN PARTS DURING MAGNETIC PARTICLE INSPECTION

[75] Inventor: Gilbert L. Marsh, Parker County, Tex.

[73] Assignee: The United States of America as represented by the Secretary of the Air Force, Washington, D.C.

[21] Appl. No.: 886,307

[22] Filed: Mar. 13, 1978

[51] Int. Cl.² .................... G01R 3/00; G01R 33/12
[52] U.S. Cl. ........................... 29/412; 29/417; 29/592 R; 324/202; 228/174
[58] Field of Search ............ 29/412, 417, 592; 324/202, 216; 228/131, 174

[56] References Cited

U.S. PATENT DOCUMENTS

| | | | |
|---|---|---|---|
| 3,582,772 | 6/1971 | Hammer | 324/202 |
| 3,591,915 | 7/1971 | Roberts et al. | 29/417 |
| 3,718,855 | 2/1973 | Rogel et al. | 324/202 |

*Primary Examiner*—Francis S. Husar
*Assistant Examiner*—Daniel C. Crane
*Attorney, Agent, or Firm*—Joseph E. Rusz; William Stephanishen

[57] ABSTRACT

The method of manufacture and use of a magnetic field sensitivity indicator apparatus for evaluating magnetic fields applied to ferromagnetic material parts during magnetic particle inspection utilizing known defect indicators to establish the strength and direction of magnetic fields in the parts under test.

8 Claims, 4 Drawing Figures

ELEVATED TEMPERATURE WORKING

METHOD OF MANUFACTURING A MAGNETIC FIELD SENSITIVITY INDICATOR APPARATUS FOR EVALUATING MAGNETIC FIELDS IN PARTS DURING MAGNETIC PARTICLE INSPECTION

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to magnetic particle inspection, and in particular to the method of determining the strength and direction of magnetic fields in parts undergoing magnetic particle inspection.

In the prior art, the methods for magnetic particle inspection of ferromagnetic parts have been developed utilizing soft iron indicators and electronic instruments to measure magnetic fields. A major disadvantage in the electronic instrument approach is that holes must be drilled in the part under test for insertion of magnetic field pick-up coils, thus sacrificing at least one part of each configuration and size. The soft iron indicator, when placed on a part during magnetic particle inspection, will indicate the magnetic field necessary to delineate a simulated flaw slit in the indicator. The magnetic field intensity derived in this manner may not have a direct relationship to that necessary to test for a given crack size in a part.

SUMMARY OF THE INVENTION

The present invention is directed to the manufacture and use of a magnetic field sensitivity indicator apparatus which utilizes small thin sensitivity indicators which can be produced from any material to correspond to the material being magnetic particle inspected. These indicators may be made with small cracks that closely resemble natural occurring defects. These simulated cracks may be produced in any length to correspond with the critical crack length of the material that is to be inspected or to other inspection criteria and specifications. During magnetic particle inspection, these sensitivity indicators may be placed on a ferromagnetic part in various directions to determine the strength and direction of magnetic fields in the part. When the simulated crack in the indicator has been delineated to its predetermined length, then the magnetic field in the part is sufficient.

It is one object of the present invention, therefore, to provide an improved method of evaluating magnetic fields in parts during magnetic particle inspection.

It is another object of the invention to provide an improved method of determining sufficiency and direction of magnetic fields in ferromagnetic parts during inspection by the magnetic particle method.

It is still another object of the invention to provide an improved method of producing and using sensitivity indicators containing simulated cracks or defects.

It is yet another object of the invention to provide an improved process of producing simulated defects in ferromagnetic test materials and the use of these test materials to indicate the strength and direction magnetic fields in parts undergoing magnetic particle inspection.

These and other advantages, objects and features of the invention will become more apparent from the following description taken in connection with the illustrative embodiment in the accompanying drawings.

DESCRIPTION OF THE PREFERRED EMBODIMENT

Figure 1:
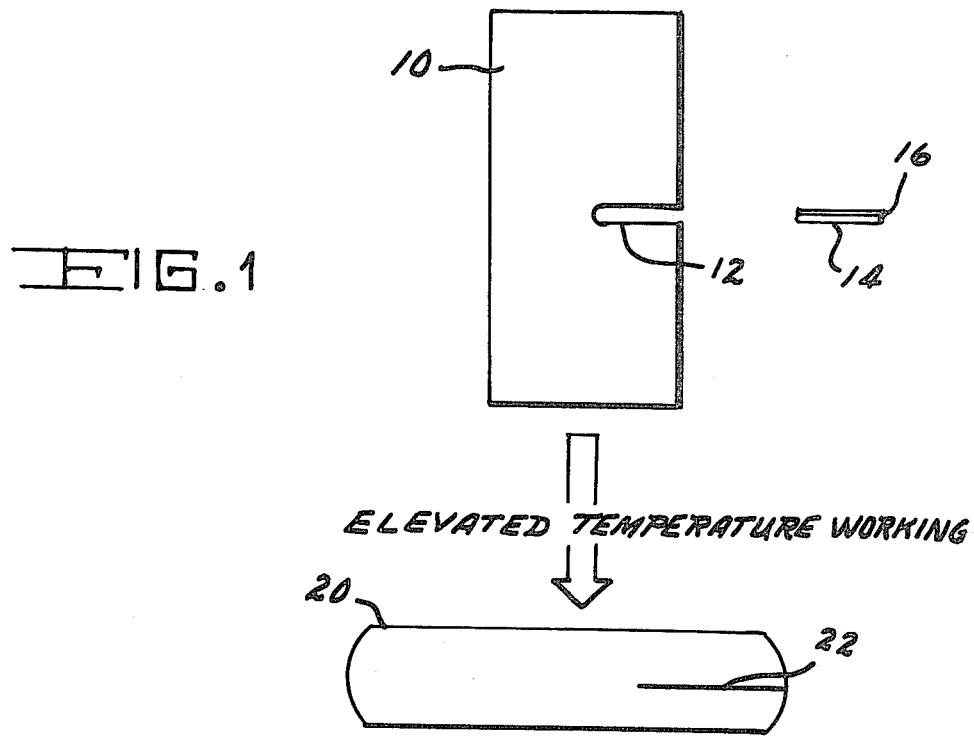
FIG. 1 is a diagrammatic illustration of the method for producing simulated cracks or defects in the sensitivity indicator materials.
Figure 2:
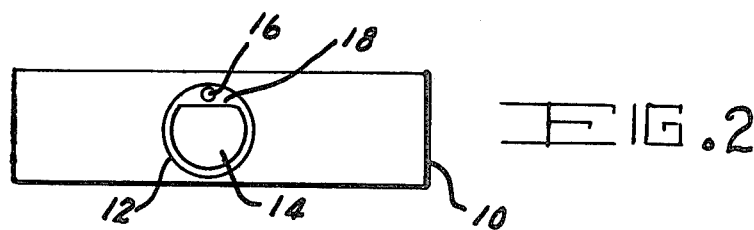
FIG. 2 is a side view in enlarged detail of the hole preparation shown in FIG. 1.

Referring now to FIG. 1, there is shown the method of making a sensitivity indicator which may be utilized in the method of evaluating magnetic fields applied to test materials or parts during magnetic particle inspection. The object material 10 which is to be used as the indicating means has a hole 12 drilled to a depth as determined by the number of sensitivity indicators that are desired. A plug 14 is made from the same type material as the object material 10. The plug 14 is dimensioned to a length approximately equal to the depth of the hole 12 and to a diameter smaller than that of the hole 12 so that a slip fit is obtained. There is shown in FIG. 2 an end view of the plug 14 having a reduced section 18 thereon, to which a piece of foreign substance 16 may be affixed. The plug 14 together with its associated foreign substance 16 are shown positioned in the hole 12. A piece of foreign substance 16 is measured and cut to the size that is determined by the desired size of the simulated crack that is to be produced. The substance 16 which is to be implanted must have such qualities that it will not diffuse into the object material and will not bond to the object material 10. Further necessary qualities are that the substance 16 must be capable of being deformed at the elevated working temperatures of the object material 10, and also be capable of being cut or shaped into small particles that can be accurately measured. The foreign substance 16 that is chosen depends upon the object material 10, for example, for iron and steel objects, glass is particularly well suited.

The method of FIG. 1 comprises the steps of producing a reduced area on the plug 14 and inserting plug 14 into the hole 12 in the object material 10 shown in FIG. 2. A piece of foreign substance 16 is cut to the same length as the plug and is inserted into the space generated between the reduced section 18 of the plug 14 and the hole 12 in the object material 10 as shown in FIG. 2. The present method further includes the steps of working the object material at elevated temperatures to weld the plug to the object material and to reduce the height of the implanted substance. This method produces as shown in FIG. 1 billets 20 with simulated cracks 22 which are very small in height and may be varied in length.

Figure 3:
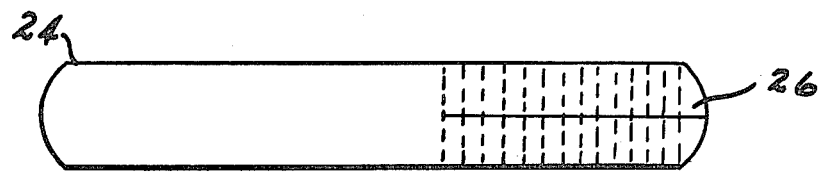
FIG. 3 illustrates the method of cutting the billet to produce individual sensitivity indicators, and FIG. 4 in an enlarged view of an individual sensitivity indicator.
Figure 4:
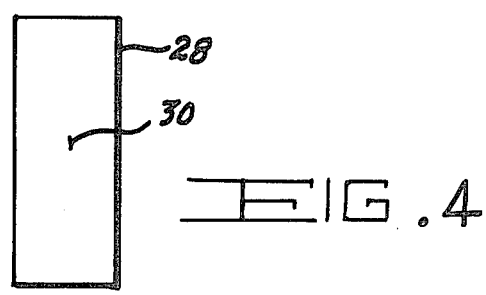

Turning now to FIG. 3, there is shown a billet 24 having a simulated crack or defect 26 on the surface thereon. The billet 24 may be sliced into as many individual sensitivity indicators as is desired. Furthermore, the individual sensitivity indicators may be dimensioned as desired or required for a particular application in the magnetic particle inspection process. Generally, the billet 24 may be cut into thin (normally 0.020" thick) slices and the surface prepared representative of the part to be magnetic particle inspected. Each slice produces a sensitivity indicator 28 having a defect 30 as shown in FIG. 4.

The present invention finds application in the evaluation of magnetic fields applied to parts during magnetic particle inspection in the following manner. The part which is to be tested may have two or more sensitivity indicators affixed to the critical areas. The indicators may be held in place with tape, or by other suitable means. When a sufficient magnetic field has been applied to the part, a black light may be used to delineate the simulated cracks in the sensitivity indicators and thus the effectiveness and direction of the magnetic field has been determined. Thus, the method of evaluating magnetic fields of the present invention is characterized by the manufacture of sensitivity indicators with simulated cracks of known size, and the placement of these indicators on a part during magnetic particle inspection. The direction and strength of magnetic fields in the part are evaluated by the delineation of the simulated cracks in the indicators.

Although the invention has been described with reference to a particular embodiment, it will be understood to those skilled in the art that the invention is capable of a variety of alternative embodiments within the spirit and scope of the appended claims.

I claim:

1. A method of producing a magnetic field sensitivity indicator comprising the steps of:
    (a) drilling a first object material to a predetermined depth to provide a hole therein,
    (b) cutting a plug to the same length and a slightly smaller diameter as the hole in said first object material,
    (c) reducing a portion of said plug along its entire length,
    (d) cutting a second material to a predetermined length,
    (e) inserting said plug into said hole in said first object material,
    (f) inserting said second material into the space between said first object material and said plug, said first object material and said second material providing a predetermined height, and
    (g) elevating the temperature of the above combination to weld said plug to said first object material and to reduce the height of the implanted second material thereby forming an indicator having a second material and plug permanently disposed in the first object material hole.

2. A method of producing a magnetic field sensitivity indicator as described in claim 1 further including the step of:
    selecting said second material to be compatible with said first object material.

3. A method of producing a magnetic field sensitivity indicator as described in claim 1 further including the step of:
    cutting the combination of said first object material, plug and second material after heating into billets.

4. A method of producing a magnetic field sensitivity indicator as described in claim 1 wherein said first object material comprises a ferromagnetic material.

5. A method of producing a magnetic field sensitivity indicator as described in claim 1 wherein said predetermined length is proportional to a desired critical crack length defect.

6. A method of producing a magnetic field sensitivity indicator as described in claim 1 wherein said plug comprises the same material as said first object material.

7. A method of producing a magnetic field sensitivity indicator as described in claim 1 wherein said predetermined depth controls the number of sensitivity indicators to be produced.

8. A method of producing a magnetic field sensitivity indicator as described in claim 3 further including the step of:
    cutting said billet into thin slices, each thin slice producing a sensitivity indicator.